US00PP31897P2

(12) United States Plant Patent
Antonissen

(10) Patent No.: US PP31,897 P2
(45) Date of Patent: Jun. 23, 2020

(54) *LEUCOTHOE* PLANT NAMED 'RANT01'

(50) Latin Name: ***Leucothoe* hybrid**
Varietal Denomination: RANT01

(71) Applicant: Ronny Antonissen, Sprundel (NL)

(72) Inventor: Ronny Antonissen, Sprundel (NL)

(73) Assignee: VAN VLIENT NEW PLANTS B.V., Stroe (NL)

( * ) Notice: Subject to any disclaimer, the term of this patent is extended or adjusted under 35 U.S.C. 154(b) by 0 days.

(21) Appl. No.: 16/602,125

(22) Filed: Aug. 7, 2019

(30) Foreign Application Priority Data

Jan. 25, 2019 (QZ) ..... PBR 2019/0241

(51) Int. Cl.
*A01H 5/00* (2018.01)
*A01H 6/36* (2018.01)

(52) U.S. Cl.
USPC ..... Plt./226

(58) Field of Classification Search
USPC ..... Plt./226, 373
CPC ... A01H 5/00; A01H 5/02; A01H 5/12; A01H 6/36
See application file for complete search history.

*Primary Examiner* — June Hwu
(74) *Attorney, Agent, or Firm* — Penny J. Aguirre

(57) ABSTRACT

A new cultivar of *Leucothoe*, 'RANT01', that is characterized by its compact plant habit and its variegated foliage with young leaves that are deep grey-orange in color with green-white margins and mature leaves that are dark green in color with white margins and changes in late summer to deep grey-orange with white margins.

2 Drawing Sheets

Botanical classification: *Leucothoe* hybrid.
Variety denomination: 'RANT01'.

BACKGROUND OF THE INVENTION

The present invention relates to a new and distinct cultivar of *Leucothoe* of hybrid origin. The new *Leucothoe* will hereafter by its cultivar name, 'RANT01'. 'RANT01' is a new cultivar of evergreen shrub grown for use as an ornamental landscape plant.

The new cultivar was discovered by the Inventor in August of 2012 as a naturally occurring branch mutation of *Leucothoe* 'Zeblid' (U.S. Plant Pat. No. 5,195) that was growing in a container in Sprundel, The Netherlands.

Asexual propagation of the new cultivar was first accomplished by the Inventor using softwood stem cuttings in September of 2012 in Sprundel, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RANT01' as a unique cultivar of *Leucothoe*.

1. 'RANT01' exhibits a compact plant habit.
2. 'RANT01' exhibits variegated foliage with young leaves that are deep grey-orange in color with green-white margins and mature leaves that are dark green in color with white margins and changes in late summer to deep grey-orange with white margins.

The parent of 'RANT01', 'Zeblid', differs from 'RANT01' in having a less compact plant habit, foliage that is non-variegated with young leaves that are red in color and mature leaves that are medium green in color. 'RANT01' can be most closely compared to *Leucothoe* 'Carnaval' (not patented) and 'Rainbow' (not patented). 'Carnaval' is similar to 'RANT01' in leaf shape and mature leaf colors. 'Carnaval' differs from 'RANT01' in having a less compact plant habit, leaves that are more irregularly variegated, and young leaves that are lighter in color. 'Rainbow' is similar to 'RANT01' in leaf variegation. 'Rainbow' differs from 'RANT01' in having a less compact plant habit, leaves that are more irregularly variegated, and young leaf colors that are bronze-green with white and pink variegation.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new cultivar. The plant in the photographs is 2.5 years old as grown outdoors in a 17-cm container in Boskoop, The Netherlands.

The photograph in FIG. 1 provides an overall view of the plant habit of 'RANT01'.

Figure 1:
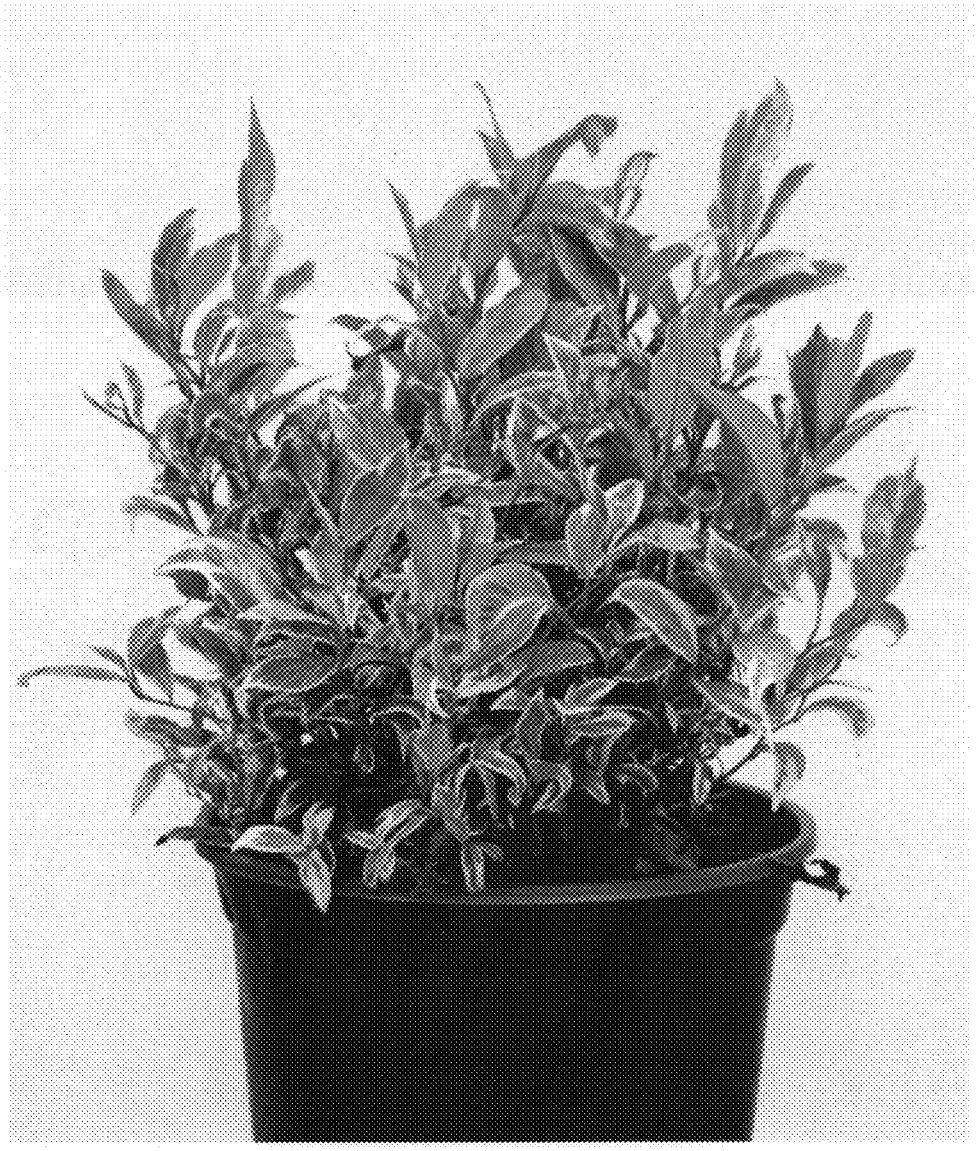
Figure 2:
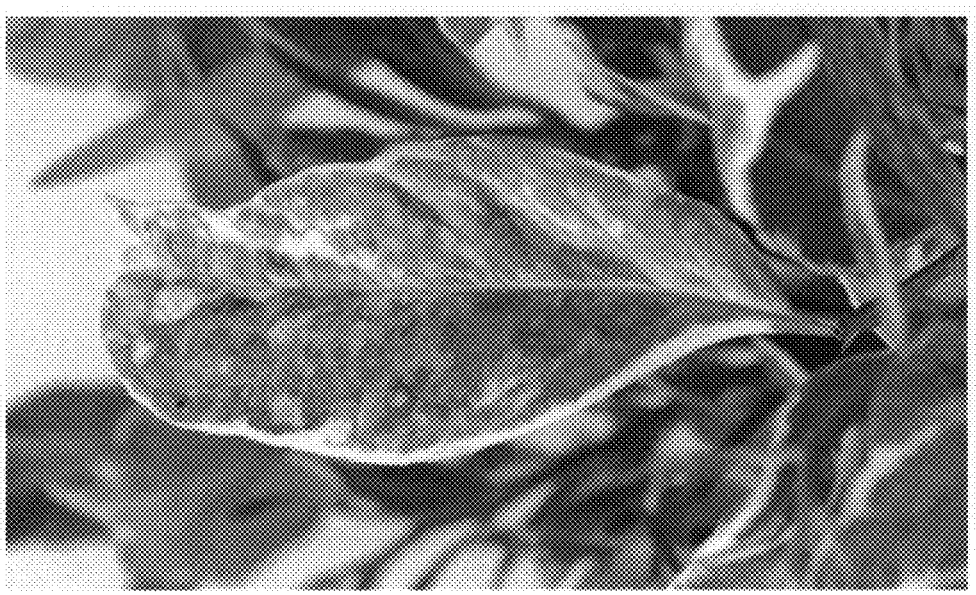

The photograph in FIG. 2 provides a close-up view of the mature foliage of 'RANT01'.

Figure 3:
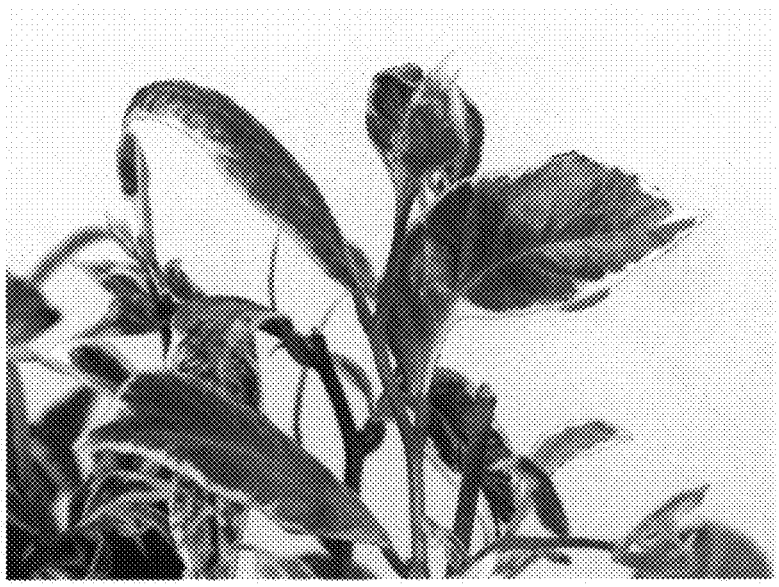

The photograph in FIG. 3 provides a close-up view of the young foliage of 'RANT01'.

The colors in the photographs may differ slightly from the color values cited in the detailed botanical description, which accurately describe the colors of the new *Leucothoe*.

DETAILED BOTANICAL DESCRIPTION

The following is a detailed description of 2.5-year-old plants of the new cultivar as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen shrub.

*Plant habit*.—Broad spreading and upright.

*Plant shape*.—Irregular, flattened globular.

*Plant size*.—Reaches about 40 cm in height and 30 cm in spread.

*Hardiness*.—At least in U.S.D.A. Zones 6 to 10.

*Diseases and pests*.—No susceptibility or resistance to diseases or pests has been observed.

*Root description*.—Slightly fibrous, average of 2 mm in diameter, dense, smooth and glabrous and 164A in color.

*Root development*.—Roots initiate in approximately 60 days, average time to produce young plant from rooted cutting is 3 months.

*Propagation*.—Softwood stem cuttings.

*Growth rate*.—Low.

Stem description:

*Shape*.—Rounded.

*Stem color*.—Young and mature branches 146D, strongly tinged 180B to 180C, older stems 146A.

*Stem size*.—An average of 15.5 cm in length and 1.5 mm in diameter.

*Stem surface*.—Slightly glossy and densely covered with very short glandular hairs; an average of 0.1 mm in length and too small to measure color.

*Stem aspect*.—Held at an average angle 40°.

*Branching*.—Very freely and densely branched, average of 22 primary branches and 40 lateral branches.

*Internode length*.—An average of 1.4 cm.

Foliage description:

*Leaf shape*.—Irregular, narrow ovate to narrow oblong and narrow obovate, often falcate.

*Leaf aspect*.—Flat to slightly convex.

*Leaf division*.—Simple.

*Leaf base*.—Attenuate.

*Leaf apex*.—Apiculate.

*Leaf venation*.—Pinnate, upper surface color 145B, lower surface color 144B.

*Leaf margins*.—Finely serrate, coarsely and irregularly angulate, unlobed.

*Leaf arrangement*.—Alternate, distichous.

*Leaf attachment*.—Petiolate.

*Leaf surface*.—Both surfaces smooth and glabrous, upper surface moderately glossy, lower surface matte.

*Leaf size*.—An average of 6 cm in length and 2.2 cm in width.

*Leaf quantity*.—An average of 12 per lateral branch.

*Leaf color*.—Young growth upper surface; 175A and 178B, finely margined 155C and 157D, new growth lower surface; 174C and 176C, finely margined 155C and 157D, mature growth upper surface; 137A, 143C and 144B, mottled and finely margined 4D and 155C, mature growth lower surface; 146C and 146D, mottled and margined 4D and 155C, older leaves upper surface; NN137A and 139A, flushed with 150D and 191A to 191D, finely margined 150D and 155C, older leaves lower surface; 191B to 191D, finely margined 4D and 155C.

*Petioles*.—About 6 mm in length and 1.75 mm in width, strong, upper surface color 145D, strongly tinged 180A, lower surface color 180C to 180D, both surfaces densely covered with very short glandular hairs an average of 0.1 mm in length and too small to measure color and matte.

Inflorescence description: No flowers observed to date.

It is claimed:

1. A new and distinct cultivar of *Leucothoe* plant named 'RANT01' as herein illustrated and described.

* * * * *